United States Patent [19]
Kriesel

[11] Patent Number: 5,433,709
[45] Date of Patent: Jul. 18, 1995

[54] FLUID DISPENSING APPARATUS INCLUDING MOUNTING BASE FOR A PLURALITY OF FLUID DISPENSING DEVICES

[75] Inventor: Marshall S. Kriesel, St. Paul, Minn.

[73] Assignee: Science Incorporated, Bloomington, Minn.

[21] Appl. No.: 156,685

[22] Filed: Nov. 22, 1993

Related U.S. Application Data

[63] Continuation-in-part of Ser. No. 53,723, Apr. 26, 1993, Pat. No. 5,354,278, which is a continuation-in-part of Ser. No. 870,521, Apr. 17, 1992, Pat. No. 5,263,940.

[51] Int. Cl.⁶ ............................................. A61M 37/00
[52] U.S. Cl. .................................................... 604/132
[58] Field of Search ............. 604/132, 131, 93, 82–85, 604/92

[56] References Cited

U.S. PATENT DOCUMENTS

| | | | |
|---|---|---|---|
| 3,468,308 | 9/1969 | Bierman | 604/132 X |
| 3,469,578 | 9/1969 | Bierman . | |
| 4,386,929 | 6/1983 | Peery et al. | 64/132 |
| 4,419,096 | 12/1983 | Leeper et al. | 604/132 |
| 4,915,693 | 4/1990 | Hessel | 604/132 |
| 4,994,031 | 2/1991 | Theeuwes | 604/85 |
| 5,106,374 | 4/1992 | Apperson et al. | 604/131 X |
| 5,122,116 | 6/1992 | Kriesel et al. | 604/89 |
| 5,188,603 | 2/1993 | Vaillancourt | 604/131 |
| 5,199,604 | 4/1993 | Palmer et al. | 604/131 X |
| 5,263,940 | 11/1993 | Kriesel | 604/132 |
| 5,354,278 | 10/1994 | Kriesel | 604/132 |

Primary Examiner—Gene Mancene
Assistant Examiner—Jeffrey A. Smith
Attorney, Agent, or Firm—James E. Brunton

[57] ABSTRACT

An infusion apparatus for delivering beneficial agents, such as drugs to a patient at substantially a constant rate. The device uniquely includes a manifold system to which a plurality of elastomeric bladder type infusion devices are connected. Each infusion device includes an internally disposed functional substrate which carries the beneficial agent so that it can be mixed with the fluid as the fluid is being introduced into the device to distend the bladder to make it an energy source for controllably dispensing the solution mixture to the manifold system and thence to a patient. The manifold system includes control valves which permit fluid from selected infusion devices to be disposed from the apparatus.

20 Claims, 3 Drawing Sheets

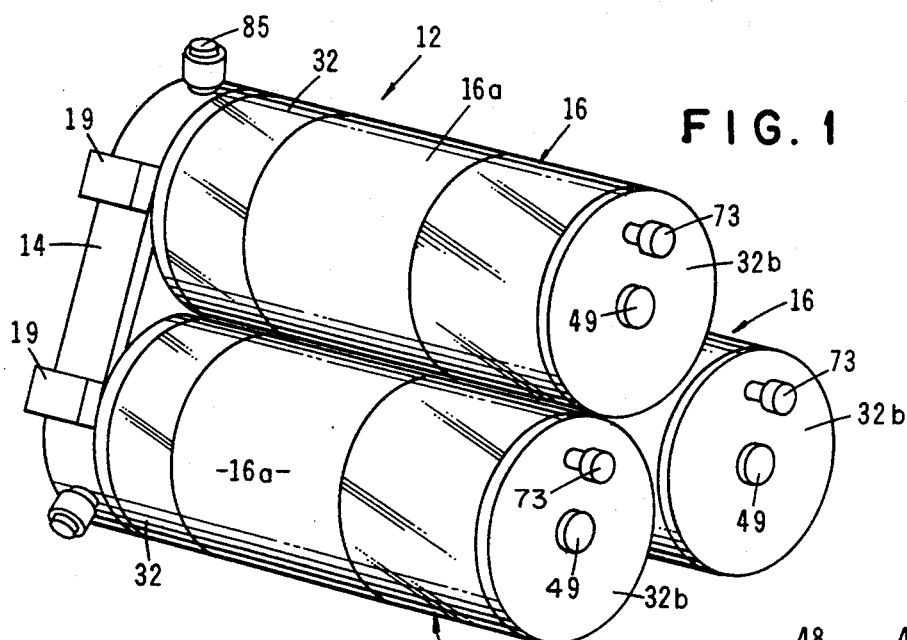
FIG. 1
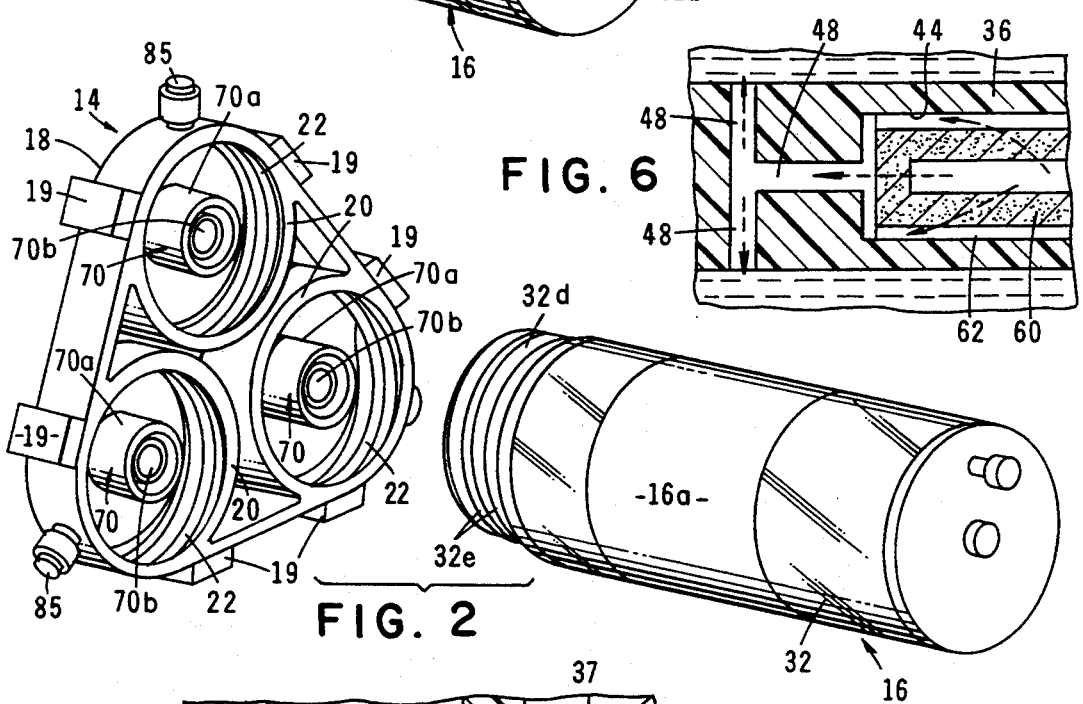
FIG. 2
FIG. 6
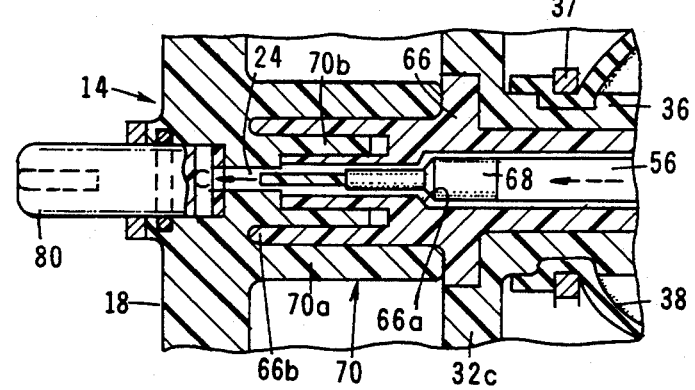
FIG. 5

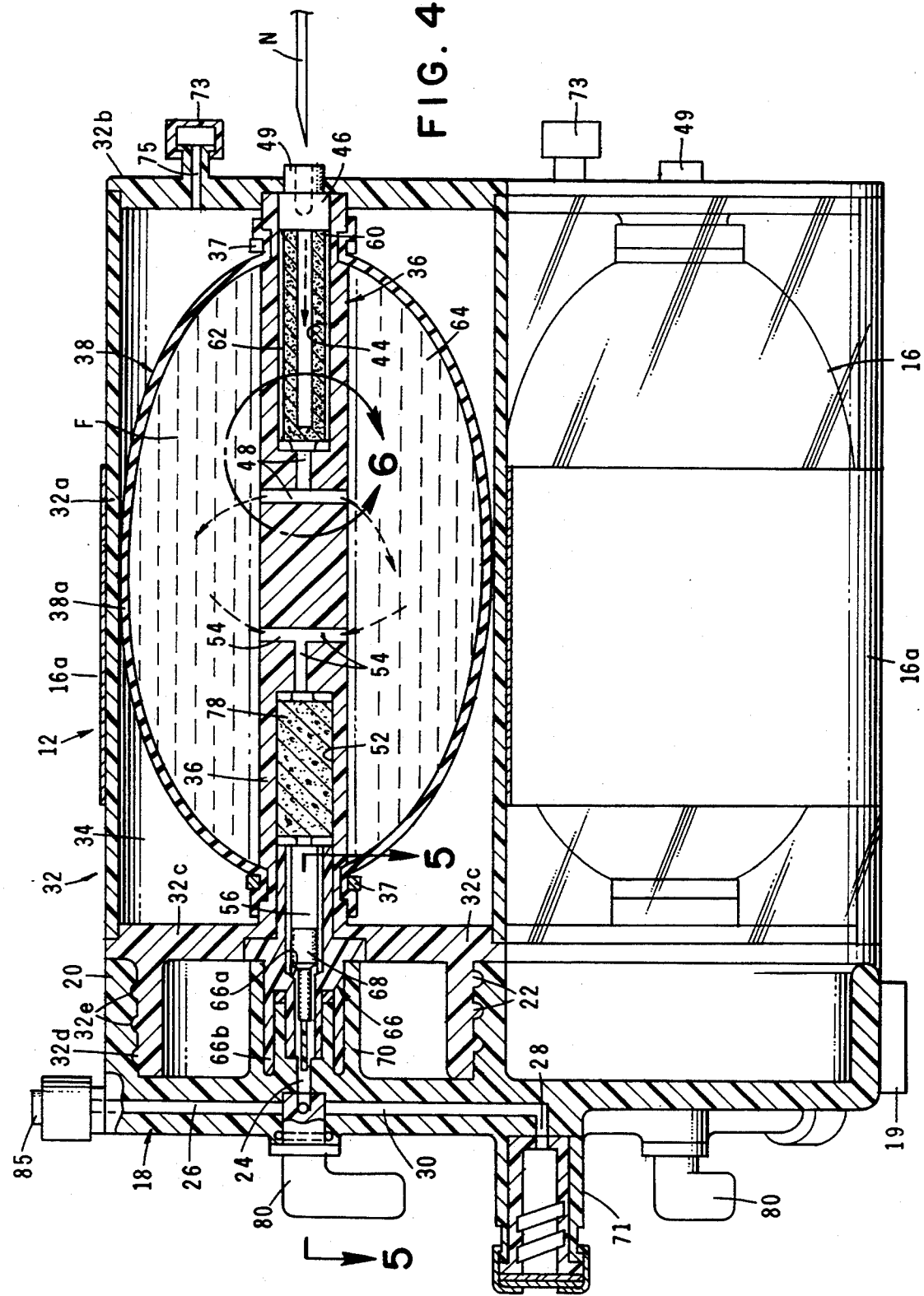

FLUID DISPENSING APPARATUS INCLUDING MOUNTING BASE FOR A PLURALITY OF FLUID DISPENSING DEVICES

BACKGROUND OF THE INVENTION

This is a Continuation-in-Part Application of co-pending U.S. application, Ser. No. 08/053,723 filed Apr. 26, 1993 (now U.S. Pat. No. 5,354,278) which is a Continuation-in-Part of application Ser. No. 07/870,521, filed on Apr. 17, 1992 (now U.S. Pat. No. 5,263,940).

1. Field of the Invention

The present invention relates generally to infusion devices. More particularly, the invention concerns an elastomeric bladder type infusion device which is used for delivering a beneficial agent to a patient at a substantially constant rate. The device uniquely includes means for intermixing a first compound, such as a drug, with a second component such as a parenteral liquid prior to delivering the solution thus formed to the patient.

2. Discussion of the Invention

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestesses the bladder in both the axial and radial directions when disposed therein, substantially filling the bladder in its unfilled state. The Hessel device also includes a one-way valve on the stress member which permits flow in the influent lumen only in the direction of the interior of the bladder.

Another type of balloon type infusion device is disclosed in U.S. Pat. No. 4,386,929 issued to Perry, et al. The Perry, et al. device has spaced apart inlet and outlet means and the bladder which is capable of expanding and contracting radially and axially upon inflation and deflation. When deflated the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated, before its subsequent inflation and deflation, substantially complete expulsion of the fluid contents of the bladder can be obtained.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time. In the device described in U.S. Pat. No. 3,469,578, the liquid is expelled solely by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tube-like member which is typically distendable both lengthwise and laterally when initially pressured. Admission and discharge of liquid is of necessity, through a single neck, or outlet portion of the balloon-like bladder.

None of the prior art devices known to applicant have the unique capability of the present invention for internally mixing a first compound, such as a drug, with a second compound such as a diluent, prior to expelling the beneficial agent thus formed from the device. Co-pending application, Ser. No. 08/053,723 describes in detail several embodiments of the invention and this last mentioned application is hereby incorporated by reference in its entirely as though fully set forth herein.

SUMMARY OF THE INVENTION

It is an object of the present invention to provide an elastomeric bladder stored energy type infusion device which can be filled with a fluid such as a diluent and which during filling efficiently mixes the diluent with an additive such as a drug or other type of beneficial agent.

More particularly, it is an object of the invention to provide an infusion device of the aforementioned character which provides the opportunity to add to the diluent or other parenteral fluid being introduced into the device selected elements, chemical compounds and biologically active materials such as drugs, medicaments, biological agents, or other therapeutic agents (additives). This addition is accomplished by removably affixing the selected additives to various forms of support structures which can be placed within the path of the fluid flowing through the device. In this way, the delivery system of the invention can be safely rendered therapeutically active upon hydration of the additive with the selected parenteral fluid.

A primary object of the present invention, as more fully described in the paragraphs which follow, is to provide a novel manifold system to which several elastomeric bladder type infusion devices of the class described in Ser. No. 08/053,723 can be operably interconnected.

Another object of the invention is to provide an apparatus which can be factory prefilled with a wide variety of medicinal fluid or one which can readily be filled in the field shortly prior to use.

Other objects of the invention are set forth in Ser. No. 08/053,723 which is incorporated herein by reference.

By way of summary description, the novel apparatus of the present invention permits the controlled delivery from the apparatus of large volumes of the same or different fluids at controlled rates in accordance with a predetermined delivery regimen. Although each of the individual fluid dispensers of the apparatus can be of varying reservoir volumes, by interconnecting a plurality of dispensers to the unique manifolding system of the invention, the controlled delivery over a given protocol of a substantial volume of fluids can readily be accomplished. The individual fluid dispensers of selected volumes are interconnected with the manifolding system by attaching the dispensers to an easily portable mounting base upon which the manifolding system is mounted. A convenient valving system permits the dispensers to be opened to the manifold system in any sequence that may be desired. The outlet port of the manifolding system is, in turn, coupled with an infusion set or other fluid transfer means for controllably transferring the fluid from the delivery apparatus to a patient, or to any other remote site.

In one form of the apparatus of the present invention, three fluid dispensers, each having an internal stored energy source, can be conveniently mounted on a portable mounting base. Filling means, which also comprises a part of the apparatus of the invention, can be used to fill, or charge, the reservoirs of the mounted fluid dispensers with any selected fluid such as a diluent or with any of a variety of beneficial agents. Through the use of the novel apparatus of the invention, multiple agents can be dispensed over time individually or in cooperation with a diluent.

BRIEF DESCRIPTION OF THE DRAWINGS

FIG. 1 is a generally perspective view of the fluid delivery device of one form of the present invention.

FIG. 2 is a generally perspective, exploded view of the device shown in FIG. 1 with one dispenser shown in a manifold connection position.

FIG. 4 is an enlarged view taken along lines 4—4 of FIG. 3.

FIG. 5 is an enlarged, cross-sectional view taken along lines 5—5 of FIG. 4.

FIG. 6 is an enlarged, cross-sectional view of the area 6 indicated in FIG. 4.

DESCRIPTION OF ONE FORM OF THE INVENTION

Figure 3:
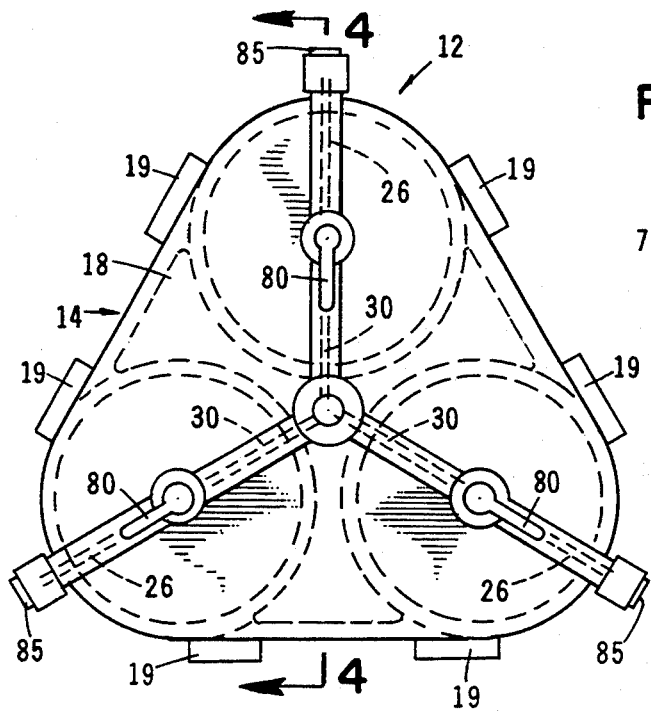
FIG. 3 is an end view of the apparatus of FIG. 1.

Referring to the drawings and particularly to FIGS. 1, 2, and 3, the apparatus of one form of the invention is there illustrated and generally identified by a numeral 12. The apparatus comprises a portable mounting base assembly 14 to which a plurality of fluid dispensers 16 can be interconnected. As best seen in FIGS. 2 and 4, the mounting base assembly 14 comprises a generally triangular shaped planar base wall 18 having a plurality of generally circular shaped, upstanding connector walls 20 connected thereto. As shown in FIG. 2, each of the connector walls 20 is provided with internal threads. Base wall 18 is provided with a plurality of first and second inlet passageways 24 and 26 which communicate with an outlet passageway 28 via a plurality of connector passageways 30 (FIG. 3). Valve means, which are of a character presently to be described, are in communication with outlet passageway 28 and function to control the flow of fluid from passageways 24 and 26 toward outlet passageway 28. A plurality of supporting feet 19 are provided along the periphery of base wall 18.

In the form of the invention shown in FIGS. 1 through 6, three fluid dispensers 16 are connected to mounting base assembly 14. Each fluid dispenser 16 comprises an elongated housing 32 having an internal chamber 34, a support 36 disposed within internal chamber 34 and extending longitudinally of the housing 32, and a generally cylindrically shaped, elongated elastomeric member 38. A medicament label 16a is provided on each fluid dispenser 16.

Housing 32 comprises a cylindrically shaped central portion 32a and inlet and outlet end plates 32b and 32c respectively. Central section 32a and end plates 32b and 32c may be constructed of any suitable rigid plastic material such as a polycarbonate and end plates 32b and 32c can be affixed to the central section by any suitable means such as adhesive bonding or an appropriate sonic weldment. Elastomeric member 38 is securely affixed proximate its ends to support 36 by means of suitable ring clamps 37 such as self-locking plastic panduit strips.

As best seen by referring to FIG. 4, support 36 is provided with a first chamber 44 having a fluid inlet 46 and a fluid outlet 48 (see also FIG. 6). Fluid inlet 46 is accessible via filling means here shown as a septum 49. Septum 49 can be constructed from a self-sealing, non-coring material such as silicone SEBS, which can be sealably punctured by a needle of a conventional syringe, or may be provided with a slit adapted to accept a blunt cannula of a character well know to those skilled in the art. Septum 49 is receivable within one end of chamber 44 and extends through end wall 32b of housing 32 in the manner shown in FIG. 4. Support 36 is also provided with a second chamber 52 having fluid passageways 54 and an outlet fluid passageway 56. It is to be observed that elastomeric member 38 includes a central portion generally designated as 38a which overlays fluid outlet passageway 48 and fluid inlet passageways 54 of support 36.

As discussed in detail in co-pending Ser. No. 08/053,723, which is incorporated hereby by reference, the dispensing device of the invention is unique in that it provides an opportunity to add to a diluent or other parenteral fluid that is introduced into the device via septum 49, selected elements, chemical compounds and biologically active materials such as drugs, medicaments, biological agents and other therapeutic agents (additives). This addition is accomplished by removably affixing selecting additives to various forms of support structures which can be placed into chamber 44 of support member 36 so that they reside within the path of the fluid flowing through inlet fluid passageway 46 and outlet passageway 48 of support member 36. Reference should be made to Ser. No. 08/053,723 for the definition of the following terms: Element; Additive; Beneficial Agents; Biologically Active Materials; Adding Means, and Additive Presentation Means.

In using the apparatus of the invention, septum or noncoring injection site 49 is penetrated by needle "N" of a syringe (FIG. 4) and a parenteral fluid, such as a sterile diluent, is introduced into inlet passageway 46 using the needle syringe. As indicated by the arrows in FIG. 4, as the diluent flows longitudinally of inlet passageway 46 it will pass through porous member 60, into flow channels 62 which surround member or substrate 60 and then into fluid reservoir 64 (FIG. 4) via outlet passageway 48. This diluent flow under pressure will urge bladder 38 outwardly into the position shown in FIG. 4 and, in so doing, will impart internal stresses which tend to continuously urge the bladder toward a less distended configuration.

As the liquid flow through porous member 60, the additives presented to the liquid will be releasably separated from the member and added to the flow, or solubilized by the diluent, thereby activating the diluent to form the therapeutic solution to be dispensed to the patient.

The various types of parenteral fluid and the numerous forms of adding means or additive assemblies illustrated and described in Ser. No. 08/053,723 can readily be used in the apparatus of the present invention. These various fluids and adding means are intended to merely exemplify, not to limit, the wide variety of materials, constructions and techniques for affinity and separation that can be used to introduce the desired additives into the liquid introduced into the inlet flow passageway 46 of the device via septum 49.

After the diluent or other parenteral fluid is introduced into the fluid dispensers and mixed with the additive contained therein, the fluid dispensers can be interconnected with portable mounting base assembly 14 in the manner shown in FIGS. 1 and 2. In this regard it is to be noted that wall 32c of each of the dispenser housings 32 is provided with an outwardly extending wall 32d having external threads 32e. Threads 32e are mateable with threads 22 provided on the mounting base so that the fluid dispensers can be readily coupled with the mounting base to form the construction shown in FIG. 4.

As best seen in FIGS. 4 and 5, support member valve means are provided on forward wall 32c of each fluid dispenser 16 for controlling the flow of fluid between outlet passageway 56 of the dispenser and one of the first inlet passageway 24 of the mounting base assembly. This valve means here comprises a valve body 66, which is connected to wall 32c and extends outwardly therefrom, and a valve member 68, which is reciprocally movable within body 66. Body 66 is provided with a valve seat 66a which is sealably engaged by valve member 68 when the member is in a first closed position.

Referring to FIGS. 2 and 5, in order to permit precise coupling of the fluid dispensers with the mounting base, wall 18 is provided with a plurality of upstanding, socket like protuberances 70 which closely receive valve bodies 66 of the fluid dispensers. Protuberances 70 comprise a part of the support member valve operating means of the invention and each includes an outer, generally cylindrical wall 70a and an inner concentric, cylindrical wall 70b within which is mounted a valve operating stem 72 (FIG. 5). Stem 72 engages valve member 68 as each fluid dispenser is threadably coupled with the mounting base assembly and, as shown in FIG. 5, moves valve member 68 into a second valve open position, thereby permitting fluid flow from outlet passageway 56 into inlet passageway 24 of the mounting base. To guide movement of the valve body into the socket-like protuberance 70, each valve body includes a skirt-like portion 66b which is closely received between cylindrical walls 70a and 70b of the protuberances 70.

After each fluid dispenser is coupled with the base assembly so that each valve member 68 is in the open position shown in FIG. 4, fluid can be transferred to the mounting base assembly and then to a patient or to a remote site via a transfer tube (not shown) which is appropriately connected to a connector 71, provided on base wall 18. Connector 71 can be a luer connector or any other suitable connector of a character well known in the art. The fluid transfer step is accomplished by first removing the protective caps 73 which cover the venting ports 75 which are provided in each end wall 32b and then by selectively opening one or more of the mounting base valve means, or rotating control valves 80, which are mounted on base wall 18. As best seen in FIG. 4, control valves 80 are disposed intermediate first and second inlet passageways 24 and 26 and outlet passageway 28 and function to control the flow of fluid toward the outlet passageway.

Upon opening a selected one of the control valves 80, the bladder 38 of the dispenser associated with that control valve will move toward its less distended, initial starting position thereby urging the fluid "F" contained within reservoir of that dispenser through passageways 54 of the support 36. The fluid "F" which is now the diluent mixed with the additive, will flow into chamber 52 and through a flow a rate control means shown here as a porous rate control filter 78. Filter 78 can be constructed from a porous ceramic or other suitable porous plastic material such as polysulfone and can be provided with the desired porosity in a manner well known to those skilled in the art.

Fluid flowing through filter 78 will next flow into passageway 56, past valve member 68 and into inlet passageway 24 of the mounting base assembly which is associated with the open control valve 80. Next, the fluid will flow past the control valve 80 and into the associated passageway 30 and thence into outlet passageway 28. From passageway 28, the fluid will flow through connector 71 and outwardly of the apparatus.

Fluid can also be introduced into the mounting base assembly via auxiliary septums 85 mounted on base wall 18 and in communication with second inlet passageways 26. Septums 85 can be constructed from a self-sealing, non-coring material such as silicone SEBS, which can be sealably punctured by a needle of a conventional syringe or they may be provided with a slit adapted to accept a blunt cannula of a character well known to those skilled in the art. By appropriate operation of control valves 80, fluid added via septums 85 can be intermixed with fluid flowing into the mounting base from the fluid dispensers or it can flow directly to outlet passageway 28 via connector passageways 30. The fluid added via septums 85 can be a diluent or any type of beneficial agent of the character defined in Ser. No. 08/053,723.

Figure 9:
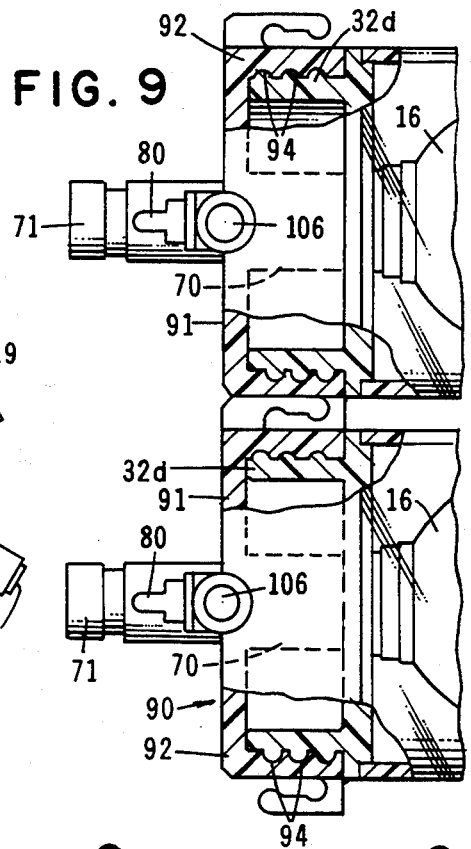
FIG. 9 is a cross-sectional view taken along lines 9—9 of FIG. 8.
Figure 7:
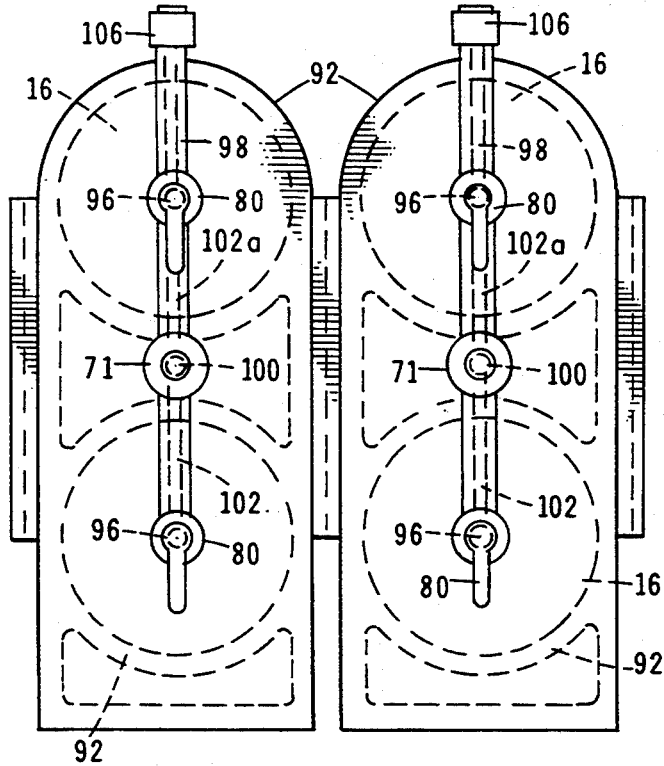
FIG. 7 is an end view of an alternate embodiment of the invention.
Figure 8:
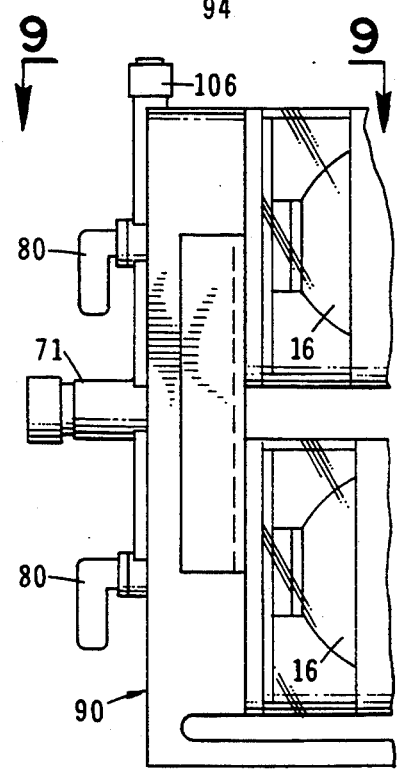
FIG. 8 is a fragmentary, side-elevational view of the apparatus shown in FIG. 7.

Referring now to FIGS. 7 through 9, another form of the invention is there shown. This form of the invention is similar in many respects to that previously described herein and like numerals are used to identify like components. More particularly, the fluid dispensers 16 are of identical construction to those shown in FIGS. 1 through 6. However, in this latest form of the invention, the mounting base assembly is constructed to accept four dispensing units 16.

In this alternate embodiment of the invention, the mounting base assembly 90 includes a generally rectangular planar base wall 91 having a plurality of generally circular shaped, upstanding connector walls 92 connected thereto. As shown in FIG. 9, each of the connector walls 92 is provided with internal threads 94. As before, base wall 90 is provided with first and second inlet passageways 96 and 98 which communicate with a pair of outlet passageways 100 via a plurality of connector passageways 102 (FIG. 7). Valve means, which are of a character previously described, are in communication with outlet passageways 100 and function to control the flow of fluid from passageways 96 and 98 toward outlet passageways 100.

In the form of the invention shown in FIGS. 7 through 9, four fluid dispensers 16 of the character previously described are connected to mounting base assembly 90.

As before, base wall 91 is provided with a plurality of upstanding, socket like protuberances 70 which closely receive valve bodies 66 of the fluid dispensers. Protuberances 70 comprise a part of the support member valve operating means of the invention and each includes a valve operating stem 72 of the character previously described. Stem 72 engages valve member 68 as each fluid dispenser is threadably coupled with the mounting base assembly and, as before moves valve member 68 into a second valve open position thereby permitting fluid flow from outlet passageway 56 thereof into one of the inlet passageways 96 of the mounting base.

After each fluid dispenser is coupled with the base assembly so that each valve member 68 is in the open position, fluid can be transferred to the mounting base assembly 90 and then to a patient or to a remote site via a transfer tube (not shown) which is appropriately connected to one of two connectors 71, provided on base wall 91. The fluid transfer step is accomplished as before by first removing the protective caps 73 which cover the venting ports 75 which are provided in each end wall 32b and then by selectively opening one or more of the mounting base valve means, or rotating control valves 80, which are mounted on base wall 91. As best seen in FIG. 7, control valves 80 are disposed intermediate first and second inlet passageways 96 and 98 and outlet passageway 100 and function to control the flow of fluid toward the outlet passageway.

Upon opening a selected one of the control valves 80, the bladder 38 of the dispenser associated with that control valve will move toward its less distended, initial starting position thereby urging the fluid "F" contained within reservoir of that dispenser outwardly of the apparatus in the manner previously described.

Fluid can also be introduced into mounting base assembly 90 via auxillary septums 106 carried by the base assembly and in communication with second inlet passageways 98. Septums 106 can be constructed from a self-sealing, non-coring material such as silicone SEBS, which can be sealably punctured by a needle of a conventional syringe or they may be provided with a slit adapted to accept a blunt cannula of a character well known to those skilled in the art. By appropriate operation of control valves 80, fluid added via septums 106 can be intermixed with fluid flowing into the mounting base from the fluid dispensers or it can flow directly to outlet passageway 100 via connector passageways 102 identified in FIG. 7 as 102a.

The materials used in the construction of the fluid dispensers 16 is discussed in detail in Ser. No. 08/053,723. The material used in the construction of mounting base assemblies 14 and 90 can be polycarbonate or any suitable rigid material with characteristics similar to polycarbonate.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid dispensing apparatus comprising:
    (a) a mounting base having first and second fluid inlets, a fluid outlet in communication with said fluid inlets, and valve means in communication with said fluid outlet for controlling fluid flow through said outlet; and
    (b) at least two fluid dispensing devices connected to said mounting base, each said device comprising:
        (i) a housing having walls defining an internal chamber and support means for supporting a stored energy source within said internal chamber, said housing also having connection means for connecting said housing to said mounting base, said support means having a fluid inlet and a fluid outlet in communication with one of said first and second fluid inlets of said base; and
        (ii) filling means for introducing fluid into said fluid inlet of said support means; and
        (iii) a generally tubular shaped elastomeric member connected proximate its ends to said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position.

2. A fluid dispensing apparatus as defined in claim 1 further comprising adding means in communication with said fluid outlet of said support means for adding an additive to fluid introduced by said filling means.

3. An apparatus as defined in claim 2 in which said adding means comprises a container.

4. An apparatus as defined in claim 2 in which said additive comprises a beneficial agent.

5. An apparatus as defined in claim 2 in which said additive comprises a biologically active material.

6. An apparatus as defined in claim 1 in which said mounting base includes first and second threaded portions and in which said connection means comprises a threaded portion on said housing for threadable interconnection with one of said first and second threaded portions on said base.

7. An apparatus as defined in claim 1 in which said mounting base includes base filling means comprising an injection port and a first fluid passageway in communication with said fluid outlet of said mounting base for introducing fluid into said first fluid passageway.

8. An apparatus as defined in claim 1 in which said support means of each said fluid dispensing device comprises an elongate support member having an inlet chamber and an outlet chamber.

9. An apparatus as defined in claim 8 in which each said fluid dispensing device further includes support valve means disposed in said outlet chamber for controlling fluid flow toward said fluid inlets of said mounting base.

10. A fluid dispensing apparatus comprising:
    (a) a portable mounting base having:
        (i) a plurality of fluid inlet passageways; and
        (ii) a fluid outlet passageway in communication with said fluid inlet passageways; and
    (b) a plurality of fluid dispensing devices connected to said base, each said device comprising:
        (i) a housing having walls defining an internal chamber and an elongated support member for supporting a stored energy source within said internal chamber, said housing also having connection means for connecting said housing to said mounting base, said support member having a fluid inlet chamber and a fluid outlet chamber in communication with one of said first and second fluid inlet passageways of said base;

(ii) filling means for introducing fluid into said fluid inlet chamber of said support member;

(iii) a generally tubular shaped elastomeric member connected proximate its ends to said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position; and (iv) adding means carried by said support means for adding an additive to fluid introduced by said filling means, said adding means comprising a beneficial agent disposed within said fluid inlet chamber of said support member.

11. A fluid dispensing apparatus as defined in claim 10 in which said portable mounting base further includes base valve means for controlling fluid flow through said fluid outlet passageway of said base.

12. A fluid dispensing apparatus as defined in claim 10 in which each said fluid dispensing device further includes support member valve means disposed within said outlet chamber of said support member for controlling the flow of fluid toward said fluid inlet passageways of said portable base.

13. A fluid dispensing apparatus as defined in claim 12 in which said connection means comprises external threads and in which said portable mounting base comprises a base wall and a plurality of upstanding, internally threaded connection walls connected to said base wall for threadably receiving said external threads of said connection means.

14. A fluid dispensing apparatus as defined in claim 13 in which said portable mounting base further included valve operating means for operating said support member valve means of said fluid dispensing apparatus.

15. A fluid dispensing apparatus as defined in claim 14 in which said support member valve means comprises a valve body having a valve seat and a valve member movable from a first position in sealing engagement with said valve seat to a second valve operating position.

16. A fluid dispensing apparatus as defined in claim 15 in which said valve operating means comprises a valve operating stem connected to said mounting base for engagement with said valve member upon threadable engagement of external thread of said fluid dispensers with said threaded connection walls of said mounting base.

17. A fluid dispensing apparatus comprising:
(a) a portable mounting base having:

(i) a plurality of first and second fluid inlet passageways;

(ii) at least one fluid outlet passageway in communication with said first and second fluid inlet passageways;

(iii) base valve means in communication with said fluid inlet and outlet passageways for controlling fluid flow toward said fluid outlet passageway; and (iv) means for injecting fluid into said second fluid inlet passageways; and (b) a plurality of fluid dispensing devices connected to said base, each said device comprising:

(i) a housing having walls defining an internal chamber and an elongated support member for supporting a stored energy source within said internal chamber, said housing also having connection means for connecting said housing to said mounting base, said support member having a fluid inlet chamber and a fluid outlet chamber in communication with said first fluid inlet passageways of said base;

(ii) support member valve means carried by said support member for controling the flow of fluid through said fluid outlet chamber;

(iii) filling means for introducing fluid into said fluid inlet chamber of said support member;

(iv) a generally tubular shaped elastomeric member connected proximate its ends to said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position; and (v) adding means carried by said support means for adding an additive to fluid introduced by said filling means, said adding means comprising a beneficial agent disposed within said fluid inlet chamber of said support member.

18. A fluid dispensing apparatus as defined in claim 17 in which said support member valve means comprises a valve body having a valve seat and a valve member movable from a first position in sealing engagement with said valve seat to a second valve open position.

19. A fluid dispensing apparatus as defined in claim 18 in which said portable mounting base further includes valve operating means for operating said support member valve means of said fluid dispensing apparatus.

20. A fluid dispensing apparatus as defined in claim 19 in which said valve operating means comprises a valve operating stem connected to said mounting base for engagement with said valve member upon threadable engagement of external thread of said fluid dispensers with said threaded connection walls of said mounting base.

* * * * *